(12) United States Patent
Kunschak

(10) Patent No.: US 11,241,567 B2
(45) Date of Patent: Feb. 8, 2022

(54) VALVE DEVICE FOR A MEDICAL FLUID LINE SYSTEM

(71) Applicant: B. BRAUN MELSUNGEN AG, Melsungen (DE)

(72) Inventor: Ralf Kunschak, Willisau (CH)

(73) Assignee: B. BRAUN MELSUNGEN AG, Melsungen (DE)

( * ) Notice: Subject to any disclaimer, the term of this patent is extended or adjusted under 35 U.S.C. 154(b) by 285 days.

(21) Appl. No.: 16/128,926

(22) Filed: Sep. 12, 2018

(65) Prior Publication Data

US 2019/0099595 A1  Apr. 4, 2019

(30) Foreign Application Priority Data

Oct. 4, 2017 (DE) .......................... 102017217634.2

(51) Int. Cl.
*A61M 39/24* (2006.01)
*A61M 39/22* (2006.01)
(Continued)

(52) U.S. Cl.
CPC .......... *A61M 39/24* (2013.01); *A61M 39/223* (2013.01); *A61M 39/227* (2013.01);
(Continued)

(58) Field of Classification Search
CPC .. A61M 39/223; A61M 39/227; A61M 39/24; A61M 2039/242;
(Continued)

(56) References Cited

U.S. PATENT DOCUMENTS

| 2,986,098 A | 5/1961 | Trout et al. |
| 3,822,720 A | 7/1974 | Souza |

(Continued)

FOREIGN PATENT DOCUMENTS

| CN | 101309719 A | 11/2008 |
| EP | 1954343 B1 | 1/2012 |
| WO | 9206732 A1 | 4/1992 |

OTHER PUBLICATIONS

Search Report received in European Application No. 18190374.1-1122 dated Feb. 19, 2019, with translation, 21 pages.
(Continued)

*Primary Examiner* — Shefali D Patel

(57) ABSTRACT

A valve device for a medical fluid line system includes a main body, the main body having a first fluid passage and a second fluid passage, each fluid passage of the first and second fluid passages extending between an inlet side and an outlet side of the main body. The main body has a first wall portion and a second wall portion which are each elastically displaceable, under an effect of fluid pressure, relative to a substantially dimensionally stable web portion of the main body. Each wall portion of the first and second wall portions is arranged on the web portion, forming one of the first and second fluid passages, in such a way that the first fluid passage is substantially uninfluenced by a fluid-pressure-induced deformation of the second wall portion, and the second fluid passage is substantially uninfluenced by a fluid-pressure-induced deformation of the first wall portion.

15 Claims, 2 Drawing Sheets

Figure 1:
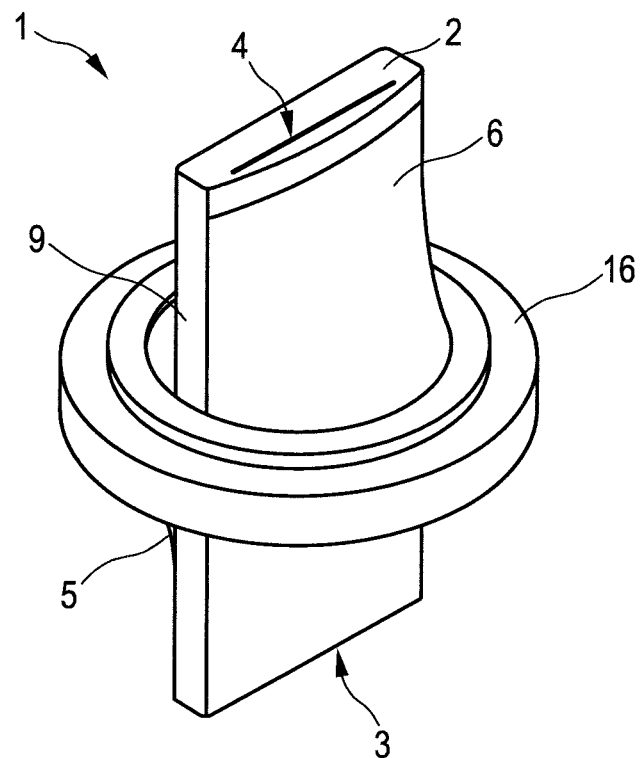

(51) Int. Cl.
*F16K 15/14* (2006.01)
*F16K 17/18* (2006.01)

(52) U.S. Cl.
CPC ..... *F16K 15/147* (2013.01); *A61M 2039/242* (2013.01); *A61M 2039/2406* (2013.01); *A61M 2039/2426* (2013.01); *A61M 2039/2433* (2013.01); *A61M 2039/2493* (2013.01); *F16K 17/18* (2013.01)

(58) Field of Classification Search
CPC .. A61M 2039/2426; A61M 2039/2433; A61M 2039/2493; A61M 2039/2406; A61M 2205/0216; F16K 15/147; F16K 15/185; F16K 17/02; F16K 17/18
See application file for complete search history.

(56) References Cited

U.S. PATENT DOCUMENTS

| | | | |
|---|---|---|---|
| 4,332,249 | A | 6/1982 | Joslin |
| 5,156,600 | A | 10/1992 | Young |
| 5,224,938 | A | 7/1993 | Fenton, Jr. |
| 9,044,541 | B2 * | 6/2015 | Blanchard ......... A61M 5/16881 |
| 2004/0176703 | A1 | 9/2004 | Christensen et al. |
| 2013/0160866 | A1 | 6/2013 | Zinn et al. |

OTHER PUBLICATIONS

Search Report received in German Application No. 10 2017 217 634.2 dated May 23, 2018, with translation, 11 pages.
Office Action received in Chinese Application No. 201811132153.6 dated Sep. 28, 2021, with translation, 17 pages.

* cited by examiner

VALVE DEVICE FOR A MEDICAL FLUID LINE SYSTEM

CROSS REFERENCE TO RELATED APPLICATION(S)

This application claims the benefit of priority under 35 U.S.C. § 119 of German Patent Application No. 10 2017 217 634.2, filed Oct. 4, 2017, the content of which is incorporated by reference herein in its entirety.

FIELD

The present disclosure relates to a valve device for a medical fluid line system, with a main body, which is configured to be flexible at least in part, and with a first fluid passage and a second fluid passage which each extend between an inlet side and an outlet side of the main body, wherein the main body is configured in such a way and the fluid passages are arranged in such a way that, in the event of a fluid overpressure between the inlet side and the outlet side, the first fluid passage is freed by means of a fluid-overpressure-induced elastic deformation of the main body and the second fluid passage is sealed off in a fluid-tight manner and, in the event of a fluid underpressure between the inlet side and the outlet side, the second fluid passage is freed by means of a fluid-underpressure-induced elastic deformation of the main body and the first fluid passage is sealed off in a fluid-tight manner, and, in the event of a neutral fluid pressure between the inlet side and the outlet side, the fluid passages are sealed off in a fluid-tight manner.

BACKGROUND

A valve device of this kind is known from US 2013/0160866 A1 and is provided for a venous catheter. Such catheters are customarily used for intravenous administration of a medical liquid or withdrawal of a body liquid. The liquid in question is injected from the catheter by an overpressure or aspirated into the catheter by an underpressure. When the catheter is not in use, the possibility of unwanted entry of body liquid into the catheter is not excluded. If it is not flushed out, the catheter can become blocked. The known valve device seeks to counteract this and for this purpose provides fluid passages that can be alternately sealed off and freed, depending on whether an overpressure or an underpressure is applied to the catheter. These fluid passages are each introduced in the form of slits into a main body in the form of a shaped silicone part. In the event of an overpressure induced by injection, a first of the slits is freed, whereas a second of the slits is sealed off. In the event of an underpressure induced by aspiration, the second slit is freed, whereas the first slit is sealed off. When the catheter is not in use, the fluid passages are sealed off. The freeing and sealing off of the slits is effected by means of a fluid-pressure-induced deformation of the shaped silicone part. In the known valve device, the slits are arranged adjacent to each other in a funnel-shaped portion of the shaped silicone part.

SUMMARY

The object of the present disclosure is to create a valve device of the aforementioned type which permits an improved sealing function and a simple design.

This object is achieved by the fact that the main body has a first wall portion and a second wall portion which are each elastically displaceable, under the effect of fluid pressure, relative to a substantially dimensionally stable web portion of the main body and are each arranged on the web portion, thereby each forming one of the fluid passages, in such a way that the first fluid passage is substantially uninfluenced by a fluid-pressure-induced deformation of the second wall portion, and the second fluid passage is substantially uninfluenced by a fluid-pressure-induced deformation of the first wall portion. By virtue of the solution according to the present disclosure, it is possible in particular to design the properties of the valve device when subjected to an overpressure to be substantially independent of the properties when subjected to an underpressure. This is because each of the fluid passages is assigned a separate wall portion. To put it simply, this permits an improved structural designability of the alternating sealing function. Thus, for example, the wall portion assigned to the first fluid passage can be displaceable with greater elastic resilience than the wall portion assigned to the second fluid passage, or vice versa. In this way, for example, the overpressure at which the first wall portion frees the first fluid passage can be structurally dimensioned independently of the underpressure at which the second wall portion frees the second fluid passage, and vice versa. In addition, the solution according to the present disclosure permits an improved structural adaptability of the volumetric flows as a function of the direction of flow through the valve device. The web portion preferably extends lengthwise parallel to a main direction of flow through the valve device. The wall portions are elastically displaceable relative to the web portion under the effect of fluid pressure, in each case between a release position, in which the respective wall portion frees the respective fluid passage, and a sealing position, in which the respective wall portion seals off the respective fluid passage. The wall portions can, for example, be configured to be elastically displaceable by the fact that they are each manufactured at least in part from a rubber-elastic material or are manufactured substantially from a non-elastic material and in this case are supported elastically resiliently on the main body. The fact that the first fluid passage is substantially uninfluenced by a fluid-pressure-induced deformation of the second wall portion signifies that current sealing or release of the first fluid passage substantially cannot be influenced by means of a purposeful deformation of the second wall portion. The same applies to the second fluid passage in connection with the first wall portion.

The solution according to the present disclosure is suitable particularly preferably for a valve device for arrangement in a catheter, in particular in a peripherally inserted central venous catheter. However, the solution according to the present disclosure is also suitable for arrangement in a lumen of any desired medical fluid line component of the kind customarily used in infusion therapy.

In one embodiment of the present disclosure, the wall portions are arranged on mutually opposite side faces of the web portion and thus separately from one another. The side faces are preferably oriented parallel to the main direction of flow through the valve device. This arrangement of the wall portions separate from each other has in particular the effect that, in the event of a fluid-pressure-induced deformation of one of the wall portions, only the fluid passage assigned to this wall portion is sealed off and/or freed.

In a further embodiment of the present disclosure, the wall portions, with respect to a sealed-off state, each bear at least in part on the web portion in the manner of a sealing lip, wherein in each case one of the fluid passages is configured in the form of a slit between the web portion, in particular the respective side face, and the respective wall portion. By contrast, with respect to a freed state, the wall portions are each elastically displaced relative to the web portion in a normal direction thereof. Provided that the wall portions are arranged on mutually opposite side faces of the web portion, the wall portions preferably bear on the respective side face (sealing position) or are lifted away from it (release position).

In a further embodiment of the present disclosure, the first fluid passage is formed between a front end of the first wall portion, directed towards the outlet side, and the web portion, and the second fluid passage is formed between a front end of the second wall portion, directed towards the inlet side, and the web portion. Accordingly, the fluid passages are preferably arranged on mutually opposite front ends of the web portion.

In a further embodiment of the present disclosure, the wall portions span the web portion, in particular the respective side face, at least partially in a curve in order to form in each case a lumen, wherein the lumen each open out at one end into the respective fluid passage. Accordingly, the wall portions are each arranged so as to be planar with respect to the web portion, in particular the respective side face, and on at least two opposite sides are connected in a fluid-tight manner to the web portion, in particular the respective side face. One of the lumen is in each case formed in this way. The lumen each extend between the inlet side and the outlet side of the main body.

In a further embodiment of the present disclosure, the lumen are each shaped in the manner of a flow nozzle and are oriented in opposite directions relative to each other fluidically, in such a way that an inlet opening of the lumen assigned to the first wall portion is oriented in the direction of the inlet side, and an inlet opening of the lumen assigned to the second wall portion is oriented in the direction of the outlet side, wherein the fluid passages each form an outlet opening of the respective lumen. Shaped in the manner of a flow nozzle signifies in particular that the lumen can each have a variable cross section of flow, with respect to a main direction of flow through the valve device. Preferably, the cross sections of flow each narrow from the respective inlet opening in the direction of the respective outlet opening or the respective fluid passage.

In a further embodiment of the present disclosure, the web portion is stiff, compared to the wall portions, and extends in the form of a flat plate substantially along a central longitudinal axis of the main body. The flat plate preferably has a rectangular basic shape, wherein the wall portions can each be arranged separately from each other on a front or rear face of the plate.

In a further embodiment of the present disclosure, the wall portions are configured to be elastically displaceable to different extents, in such a way that the fluid passages are freed and/or sealed off at quantitatively different fluid pressures. Depending on the practical application, the viscosity of a liquid to be injected through the first fluid passage may differ from the viscosity of a liquid to be aspirated through the second fluid passage. It may therefore be necessary for the fluid passages to be configured differently in such a way that they are freed and/or sealed off at different fluid pressures, in particular at markedly different fluid pressures. This embodiment of the present disclosure permits a straightforward adaptability of the valve device.

In a further embodiment of the present disclosure, the wall portions have different wall thicknesses, wall thickness profiles and/or elastic properties. For example, the first wall portion can have a thinner wall thickness compared to the second wall portion, or vice versa. Alternatively or in addition, it is possible that the wall portions have different wall thickness profiles, preferably with respect to the main direction of flow through the valve device. Alternatively or in addition, it is also possible that the first wall portion is manufactured from a different material than the second wall portion, such that these have different elastic properties. This embodiment of the present disclosure permits straightforward adaptability of the fluid pressure that is needed to displace the respective wall portion between the sealing position and the release position.

In a further embodiment of the present disclosure, the wall portions are inclined to different extents and/or extend by different lengths relative to the web portion, such that a pressure surface of the first wall portion, projected perpendicularly with respect to the inlet side, is different than a pressure surface of the second wall portion, projected perpendicularly with respect to the outlet side. The respective inclination and/or longitudinal extent accordingly influences the projected pressure surface and thus the fluid pressure at which the respective wall portion is elastically displaced under the effect of fluid pressure. This embodiment of the present disclosure permits a particularly tailored structural adaptability of the valve device.

In a further embodiment of the present disclosure, the main body has an annular profile portion which is provided for form-fit connection to an internal diameter of a medical fluid line component. The profile portion can be arranged in the form of an annular groove or in the form of an annular protuberance on the main body. Preferably, the profile portion is oriented radially with respect to a central longitudinal axis of the main body.

In a further embodiment of the present disclosure, the profile portion circumferentially engages at least in part around the web portion, approximately centrally with respect to a longitudinal extent of the web portion. Accordingly, the web portion is preferably extended by an imaginary through-opening of the annular profile portion.

In a further embodiment of the present disclosure, the wall portions are each connected to the profile portion at a front end directed away from the respective fluid passage. Accordingly, the first wall portion is connected to the profile portion at its front end directed towards the inlet side. By contrast, the second wall portion is connected to the profile portion at its front end directed towards the outlet side. This embodiment of the present disclosure is in particular especially expedient from a manufacturing point of view.

In a further embodiment of the present disclosure, the main body is configured in one piece. For example, the wall portions can be manufactured together with the web portion in the form of a one-piece injection-moulded plastic part. If a profile portion is additionally provided, the latter is preferably integrally connected to the remaining components of the main body, in particular the wall portions and the web portion. The main body can be manufactured in one piece, for example, from one and the same rubber-elastic material. Alternatively, it is possible that the web portion and the wall portions are manufactured from different materials and are thereafter connected integrally to each other by cohesive bonding.

BRIEF DESCRIPTION OF THE DRAWING FIGURES

Further advantages and features of the present disclosure will become clear from the following description of preferred exemplary embodiments, which are depicted in the drawings.

Figure 2:
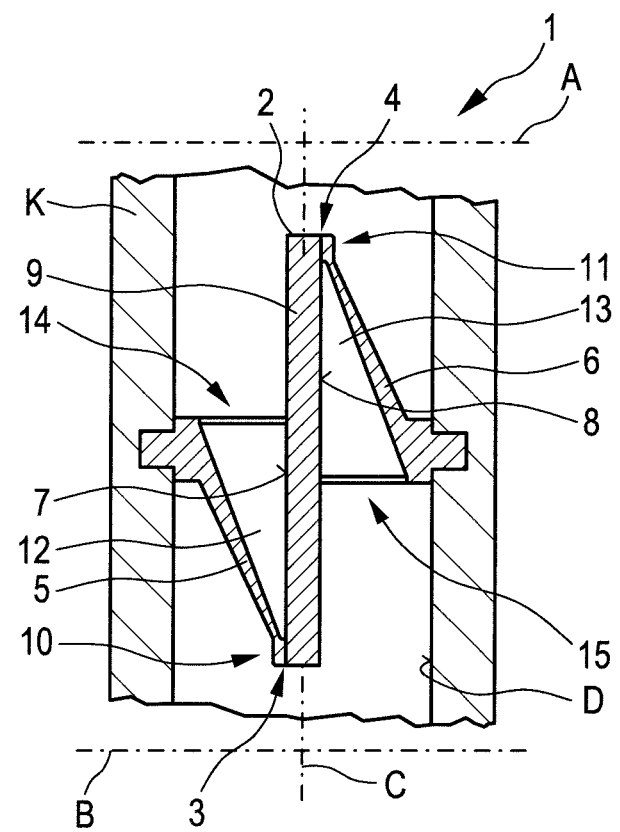
Figure 3:
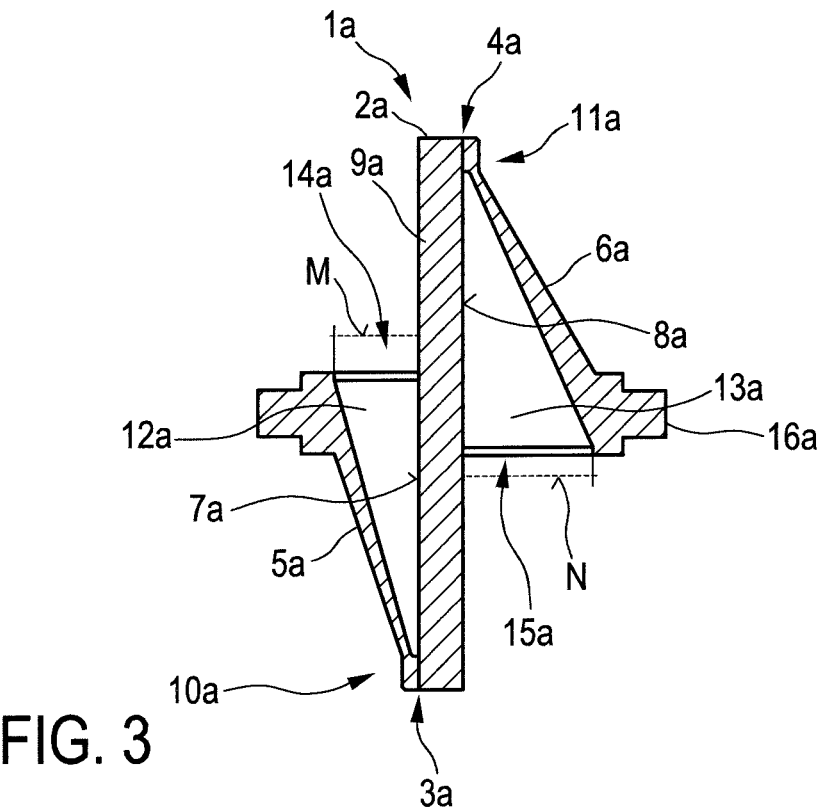
Figure 4:
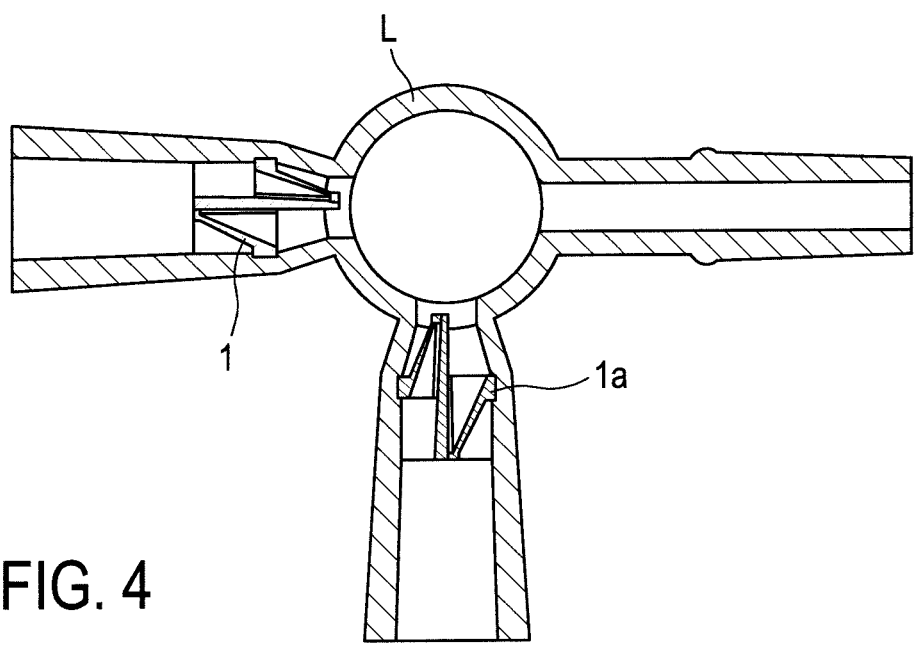

FIG. 1 shows a schematic perspective view of an embodiment of a valve device according to the present disclosure, FIG. 2 shows a schematic longitudinal sectional view of the valve device according to FIG. 1 in an installation state arranged in a lumen of a fluid line component, FIG. 3 shows, in a schematic longitudinal sectional view similar to FIG. 2, a further embodiment of a valve device according to the present disclosure, and FIG. 4 shows a longitudinal sectional view of a further fluid line component of a medical fluid line system with a first and a second valve device according to FIGS. 1 to 3.

DETAILED DESCRIPTION

The valve devices 1, 1a according to FIGS. 1, 2 and 4 and, respectively, FIGS. 3 and 4 are provided to control a flow of fluid through a lumen of a fluid line component K, L (cf. FIGS. 2 and 4) of a fluid line system.

According to FIG. 1, the valve device 1 has a main body 2 which is configured to be flexible at least in part. The main body 2 is here manufactured in one piece from a rubber-elastic material, for example a silicone elastomer. The valve device 1 moreover has a first fluid passage 3 and a second fluid passage 4, which each extend between an inlet side A and an outlet side B of the main body 2. The inlet side A and the outlet side B are each depicted schematically by dot-and-dash lines in FIG. 2. The main body 2 has a first wall portion 5 and a second wall portion 6 which are arranged on mutually opposite side faces 7, 8 of a web portion 9 of the main body 2. In a manner to be described in more detail below, the wall portions 5, 6 are each elastically displaceable relative to the web portion 9 or the respective side face 7, 8 under the effect of fluid pressure. By contrast, the web portion 9 is dimensionally stable compared to the wall portions 5, 6 and extends substantially along a central longitudinal axis C of the main body 2. As can be seen in particular from FIG. 1, the web portion 9 is configured in the form of a flat plate. The plate 9 has a rectangular shape here, although this does not necessarily have to be the case.

The first fluid passage 3 is formed between a front end 10 of the first wall portion 5, directed towards the outlet side B, and the web portion 9, more precisely the side face 7. By contrast, the second fluid passage 4 is formed between a front end 11 of the second wall portion 6, directed towards the inlet side A, and the web portion 9, more precisely the side face 8. With their respective front ends 10, 11, the wall portions 5, 6 each bear at least partially in the manner of a sealing lip on the web portion 9. In this way, the fluid passages 3, 4 are each configured in the form of a slit between the web portion 9 and the respective wall portion 5, 6. As can also be seen from FIG. 2, the wall portions 5, 6 at least partially span the respective side face 7, 8 of the web portion 9 in a curved shape (cf. FIG. 1). In this way, a lumen 12, 13 is formed in each case. The lumen 12 formed between the first wall portion 5 and the side face 7 opens at one end into the first fluid passage 3. The lumen 13 formed between the second wall portion 6 and the side face 8 opens at one end into the second fluid passage 4. The lumen 12, 13 are each shaped in the form of a flow nozzle and in this respect each have a cross section of flow that narrows in the direction of the respective fluid passage 3, 4 (cf. FIG. 2). The lumen 12, 13 are oriented in opposite directions to each other fluidically, in the sense that an inlet opening 14 of the first lumen 12 is oriented in the direction of the inlet side A and an inlet opening 15 of the lumen 13 is by contrast oriented in the direction of the outlet side B.

The main body 2 moreover has an annular profile portion 16. The annular profile portion 16 is provided in particular for form-fit connection to an internal diameter D of a medical fluid line component K, as can be seen from FIG. 2. The profile portion 16 circumferentially engages completely around the web portion 9, approximately centrally in relation to a longitudinal extent of the web portion 9. The wall portions 5, 6 are each connected to the profile portion 16 at a front end directed away from the respective fluid passage 3, 4.

FIGS. 1 and 2 each show the valve device 1 in a sealing position, such that the inlet side A is sealed off in a fluid-tight manner with respect to the outlet side B, and vice versa. In this sealing position, the wall portions 5, 6 each bear with their front ends 10, 11 on the side faces 7, 8, respectively, such that the fluid passages 3, 4 are each sealed off in a fluid-tight manner. The sealing position of the valve device 1 as seen in FIGS. 1 and 2 is adopted when there is a neutral fluid pressure between the inlet side A and the outlet side B. This is the case, for example, when the fluid line component K is not in use, i.e. when fluid is not intended to pass through the lumen of the fluid line component K in one direction or the other. In this way, the valve device 1 acts in particular against unwanted entry of a body liquid, for example blood, starting from the outlet side B to the inlet side A, such that a blockage of the fluid line component K can be avoided.

The function of the valve device 1 is explained in more detail below on the basis of a situation where there is a fluid overpressure between the inlet side A and the outlet side B and also a situation where there is a fluid underpressure between the inlet side A and the outlet side B.

A fluid overpressure between the inlet side A and the outlet side B can occur, for example, when a medical liquid is intended to be injected through the fluid line component K starting from the inlet side A. The first wall portion is then displaced relative to the web portion 9 on account of the fluid overpressure in such a way that the front end 10 is lifted from the side face 7. The slit-shaped first fluid passage 3 is widened in the normal direction of the side face 7, such that the medical liquid can be injected in the direction of the outlet side B starting from the inlet side A. At the same time, the fluid overpressure causes an elastic displacement of the second wall portion 6 with respect to the side face 8 such that the front end 11 is pressed more against the web portion 9 counter to the normal direction of the side face 8. The slit-shaped second fluid passage 4 is sealed off to a greater extent in relation to a neutral fluid pressure.

A fluid underpressure between the inlet side A and the outlet side B can occur, for example, when a body liquid is intended to be aspirated through the fluid line component K starting from the outlet side B. The second wall portion 6 is elastically displaced here relative to the web portion 9 on account of the fluid underpressure in such a way that the front end 11 is lifted from the web portion 9 in the normal direction of the side face 8. This has the effect that the second fluid passage 4 is widened in the normal direction of the side face 8. In this way, the body liquid can be aspirated through the fluid line component K starting from the outlet side B. Starting from the outlet side B, the body liquid flows through the inlet opening 15 of the lumen 13 and onwards through the second fluid passage 4 to the inlet side A. At the same time, the first wall portion 5 is elastically displaced relative to the web portion 9 on account of the fluid underpressure, in such a way that the front end 10 is pressed against the web portion 9 counter to the normal direction of the side face 7. In this way, the first fluid passage is sealed off to a greater extent in relation to a neutral fluid pressure.

By virtue of the inventive configuration of the valve device 1, the first fluid passage 3 is uninfluenced by a fluid-pressure-induced deformation of the second wall portion 6, and the second fluid passage 4 is uninfluenced by a fluid-pressure-induced deformation of the first wall portion 5. Accordingly, in particular by means of a corresponding structural configuration of the wall portions 5, 6, the valve device 1 can be adapted to a volumetric flow to be achieved during an injection and an aspiration and/or to respective opening and closing pressures.

In terms of their structural and functional features, the embodiments of inventive valve devices 1 (FIGS. 1 and 2) and 1a (FIG. 3) have a substantially similar configuration. Therefore, in order to avoid repetition with respect to the valve device 1a, reference is made to the disclosure concerning valve device 1 according to FIGS. 1 and 2. Only the essential differences between the valve device 1a according to FIG. 3 and the valve device 1 according to FIGS. 1 and 2 are discussed below. Parts and sections of the valve device 1a of identical function and/or structure are provided with the same references signs with addition of the lowercase letter a.

The valve device 1a differs substantially from the valve device 1 in that the wall portions 5a, 6a are configured to be elastically displaceable to different extents, in such a way that the fluid passages 3a, 4a are freed and/or sealed off at quantitatively different fluid pressures. For this purpose, the wall portions 5a, 6a have different wall thicknesses or wall thickness profiles. Thus, as can be seen from FIG. 3, the first wall portion 5a is thinner compared to the wall portion 6a. Accordingly, the first wall portion 5a is more elastically flexible compared to the second wall portion 6a. Alternatively or in addition, it is also possible that the wall portions 5a, 6a are produced from different materials. For example, compared to a material of the first wall portion 5a, the second wall portion 6a can be made of a stiffer material with a higher elastic modulus, or vice versa. As can also be seen from FIG. 3, the wall portions 5a, 6a are inclined to different extents with respect to the web portion 9a. The first wall portion 5a is inclined at an angle of approximately 20°, the second wall portion 6a at an angle of approximately 25°, with respect to the web portion 9a. In the present case, the wall portions 5a, 6a extend by approximately the same length. However, it is also possible that the wall portions 5a, 6a extend by different lengths. On account of the quantitatively different inclination and/or different longitudinal extent, a pressure surface M of the first wall portion 5a, projected perpendicularly with respect to the inlet side A, is different than a pressure surface N of the second wall portion 6a, projected perpendicularly with respect to the outlet side B. As an alternative or in addition to a different elastic configuration as regards the wall thicknesses and/or materials, this has the effect that the fluid passages 3a, 4a are freed and/or sealed off at quantitatively different fluid pressures.

FIG. 4 shows a further possible installation situation of the valve devices 1, 1a in a fluid line component L in the form of a three-way stopcock shown in a greatly simplified representation.

The invention claimed is:

1. A valve device for a medical fluid line system, the valve device comprising:
a main body having an inlet side and an outlet side, the main body configured to be flexible at least in part; and
a first fluid passage and a second fluid passage which each extend between the inlet side and the outlet side of the main body,
the main body configured in such a way, and the first and second fluid passages are arranged in such a way that,
in an event of a fluid overpressure between the inlet side and the outlet side, the first fluid passage is freed by a fluid-overpressure-induced elastic deformation of the main body, and the second fluid passage is sealed off in a fluid-tight manner, and,
in an event of a fluid underpressure between the inlet side and the outlet side, the second fluid passage is freed by means of a fluid-underpressure-induced elastic deformation of the main body, and the first fluid passage is sealed off in a fluid-tight manner, and,
in an event of a neutral fluid pressure between the inlet side and the outlet side, the first and second fluid passages are sealed off in a fluid-tight manner,
the main body having a first wall portion and a second wall portion which are each elastically displaceable, under an effect of a fluid pressure, relative to a substantially dimensionally stable web portion of the main body and are each arranged on the web portion, thereby each forming one of the first and second fluid passages, in such a way that the first fluid passage is substantially uninfluenced by a fluid-pressure-induced deformation of the second wall portion, and the second fluid passage is substantially uninfluenced by a fluid-pressure-induced deformation of the first wall portion,
the first wall portion and the web portion forming a first lumen therebetween, the first lumen narrowing to a minimum cross section, the minimum cross section of the first lumen adjoining and opening directly into the first fluid passage, and
the second wall portion and the web portion forming a second lumen therebetween, the second lumen narrowing to a minimum cross section, the minimum cross section of the second lumen adjoining and opening directly into the second fluid passage.

2. The valve device according to claim 1, wherein the first and second wall portions are arranged on mutually opposite side faces of the web portion and thus separately from one another.

3. The valve device according to claim 1, wherein the first and second wall portions, with respect to a sealed-off state, each bear at least in part on the web portion in a manner of a sealing lip, wherein in each case one of the first and second fluid passages is configured in a form of a slit between the web portion and one of the first and second wall portions.

4. The valve device according to claim 1, wherein the first fluid passage is formed between a front end of the first wall portion, directed towards the outlet side, and the web portion, and the second fluid passage is formed between a front end of the second wall portion, directed towards the inlet side, and the web portion.

5. The valve device according to claim 1, wherein the first and second wall portions span the web portion at least partially in a curve in order to form the first lumen and the second lumen, respectively.

6. The valve device according to claim 5, wherein the first and second lumens are each shaped in a manner of a flow nozzle and are oriented in opposite directions relative to each other fluidically, in such a way that an inlet opening of the first lumen is oriented in a direction of the inlet side, and an inlet opening of the second lumen is oriented in a direction of the outlet side, wherein the first and second fluid passages each form an outlet opening of the first and second lumens, respectively.

7. The valve device according to claim 1, wherein the first and second wall portions are configured to be elastically displaceable to different extents, in such a way that the first and second fluid passages are freed and/or sealed off at quantitatively different fluid pressures.

8. The valve device according to claim 7, wherein the first and second wall portions have different wall thicknesses, wall thickness profiles and/or elastic properties.

9. The valve device according to claim 7, wherein the first and second wall portions are inclined to different extents and/or extend by different lengths relative to the web portion, such that a pressure surface of the first wall portion, projected perpendicularly with respect to the inlet side, is different than a pressure surface of the second wall portion, projected perpendicularly with respect to the outlet side.

10. The valve device according to claim 1, wherein the main body has an annular profile portion which is provided for form-fit connection to an internal diameter of a medical fluid line component, the annular profile portion having a circumference.

11. The valve device according to claim 10, wherein the annular profile portion circumferentially engages at least in part around the web portion, centrally with respect to a longitudinal extent of the web portion.

12. The valve device according to claim 10, wherein the first and second wall portions are each connected to the annular profile portion at an end directed away from a respective fluid passage of the first and second fluid passages.

13. The valve device according to claim 10, wherein the first wall portion comprises a first partially circular end connected to a first side of the annular profile portion, and the second wall portion comprises a second partially circular end connected to a second side of the annular profile portion opposite the first side, the first partially circular end and the second partially circular end each lying inside the circumference of the annular profile portion.

14. The valve device according to claim 1, wherein the main body is configured in one piece.

15. A valve device for a medical fluid line system, the valve device comprising:

a main body having an inlet side, an outlet side, an annular portion, and a web portion; and a first fluid passage and a second fluid passage which each extend between the inlet side and the outlet side of the main body, the web portion defining a central longitudinal axis through a center of the annular portion, with the web portion extending parallel to the central longitudinal axis, the annular portion having a circumference that defines a circular plane, the web portion extending perpendicularly to the circular plane through a center of the circular plane, the main body configured in such a way, and the first and second fluid passages are arranged in such a way that, in an event of a fluid overpressure between the inlet side and the outlet side, the first fluid passage is freed by a fluid-overpressure-induced elastic deformation of the main body, and the second fluid passage is sealed off in a fluid-tight manner, and, in an event of a fluid underpressure between the inlet side and the outlet side, the second fluid passage is freed by a fluid-underpressure-induced elastic deformation of the main body, and the first fluid passage is sealed off in a fluid-tight manner, and, in an event of a neutral fluid pressure between the inlet side and the outlet side, the first and second fluid passages are sealed off in a fluid-tight manner, the main body having a first wall portion and a second wall portion, the first and second wall portions each being elastically displaceable in a radially outward direction with respect to the central longitudinal axis and the web portion under an effect of a fluid pressure, the first and second wall portions each forming one of the first and second fluid passages, in such a way that the first fluid passage is substantially uninfluenced by a fluid-pressure-induced deformation of the second wall portion, and the second fluid passage is substantially uninfluenced by a fluid-pressure-induced deformation of the first wall portion.

\* \* \* \* \*